United States Patent [19]
Zacharias, Jr.

[11] Patent Number: 4,573,346
[45] Date of Patent: Mar. 4, 1986

[54] METHOD OF MEASURING THE COMPOSITION OF AN OIL AND WATER MIXTURE

[75] Inventor: Ellis M. Zacharias, Jr., Tulsa, Okla.

[73] Assignee: Nusonics, Inc., Tulsa, Okla.

[21] Appl. No.: 514,576

[22] Filed: Jul. 18, 1983

[51] Int. Cl.[4] .................... G01N 29/02; G01F 15/08
[52] U.S. Cl. .................................. 73/61.1 R; 73/200
[58] Field of Search ............... 73/200, 61.1 R, 861.04, 73/861.28, 597; 55/55, 189, 270

[56] References Cited

U.S. PATENT DOCUMENTS

| | | | |
|---|---|---|---|
| 2,097,829 | 11/1937 | Bassler | 73/200 |
| 3,926,664 | 12/1975 | Verreydt | 55/55 |
| 4,080,837 | 3/1978 | Alexander et al. | 73/61.1 R |
| 4,236,406 | 12/1980 | Reed et al. | 73/61.1 R |
| 4,282,434 | 8/1981 | Lyman | 55/55 |

*Primary Examiner*—David L. Lacey
*Attorney, Agent, or Firm*—Head, Johnson & Stevenson

[57] ABSTRACT

A method of determining the net volume of water and oil in a flow stream, including the steps of collecting the fluid in a vessel providing a quiescent zone, venting pressure from the vessel to permit at least a portion of dissolved gas to flush from the fluid, repressuring the fluid within the vessel to a superatmospheric pressure to force any remaining entrained gas bubbles back into solution, passing the fluid from the vessel while subjected to a superatmospheric pressure through a sonic apparatus having a sonic path disposed at an angle to the flow stream to measure the upstream and downstream speed of sound transmission of the fluid, calculating from the difference in the upstream and downstream speeds of sound transmission the volume of fluid flow and from the summation of the speeds of sound transmission the fluid composition, and from these calculations the net volume of oil and water flow.

6 Claims, 1 Drawing Figure

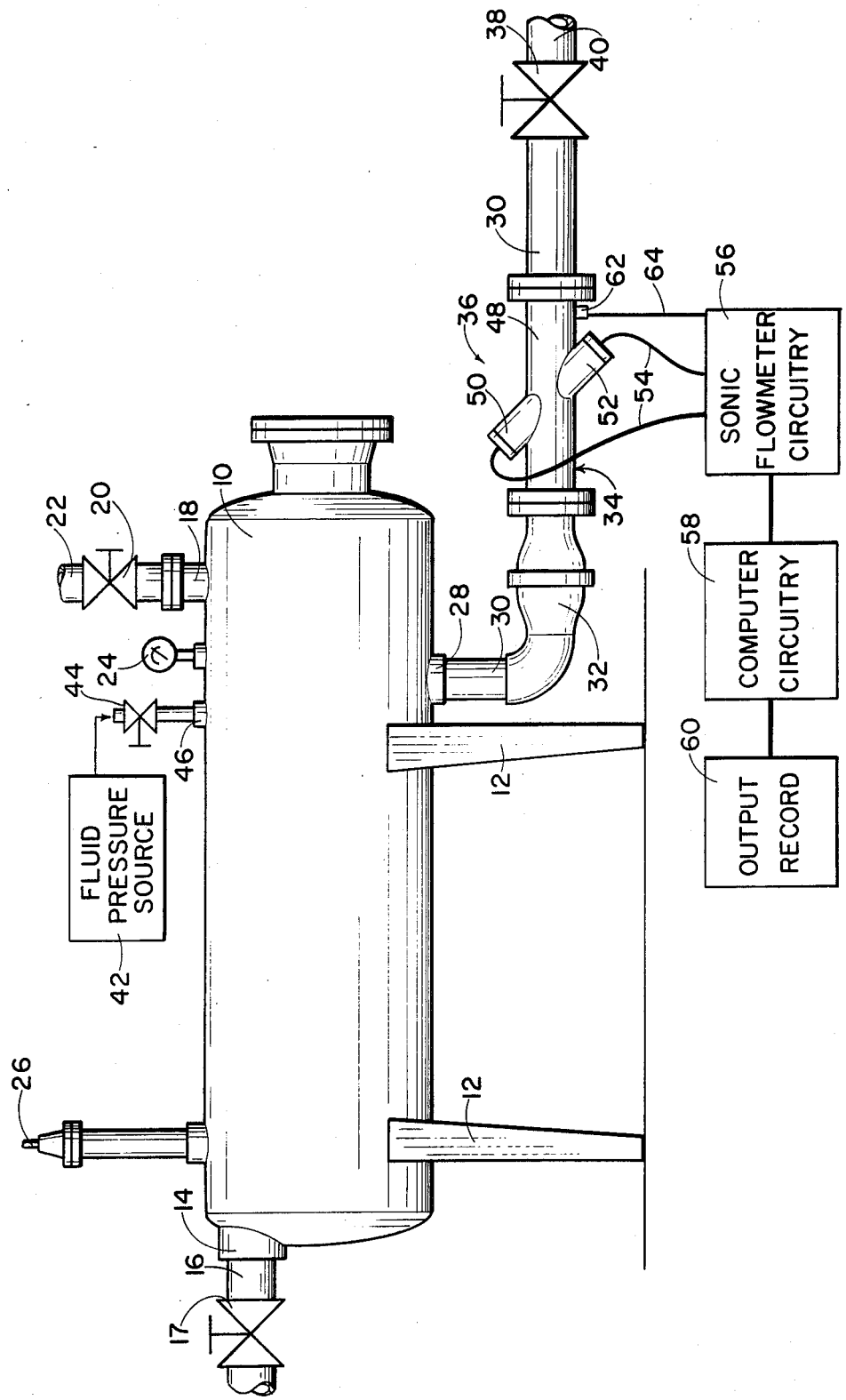

METHOD OF MEASURING THE COMPOSITION OF AN OIL AND WATER MIXTURE

BRIEF SUMMARY OF THE INVENTION

In the petroleum industry, as well as in other processing and chemical industrial applications, it is frequently necessary to be able to accurately determine in a stream flow the net amount of different components of the stream. In the petroleum industry it is frequently desirable to determine in a stream flow the net volume of water and oil making up the stream.

One method of detecting the transition in a fluid stream from water to oil or vice versa employs the use of a sonic apparatus. It is well know that the speed of sound transmission of water and oil are different and by measuring the speed of sound transmission of fluid flow in a stream the amount of water and oil making up the stream can be determined.

Others have applied the principle of the use of the speed of sound transmission to detect the transition in a fluid stream of oil to water or water to oil such as in previously issued U.S. Pat. Nos. 4,236,406 and 4,080,837. One problem however, which has existed with the present methods and apparatus, is that most crude oil includes co-mingled gas which may be in the form of entrained bubbles but which is most often carried in the stream as dissolved gas. While sonic apparatus works efficiently and effectively to measure the speed of sound transmission in fluids and can be use to readily distinguish between water and oil when the fluids are relatively gas free, the presence of gas in the stream can materially affect the measurements provided by the sonic apparatus. When gas is entrained in the fluid the sonic measurements may lead to inconclusive or erroneous indications. Since gas is so characteristicly present in crude oil the existence of entrained gas bubbles in crude oil, or in water associated with crude oil, can jeopardize the dependability of measurements made by sonic apparatus.

The present invention is directed towards a method of detecting fluid composition which substantially overcomes the problem encountered by entrained gas. In practicing the method the fluid is collected in a vessel providing a quiescent zone, that is, a zone in which the rate of fluid movement is substantially decreased. This can be accomplished by conducting the fluid from a pipeline into a vessel of a large diameter and volume relative to the pipeline. In such quiescent conditions gas entrained within the fluid is provided an opportunity to rise to the top of the fluid within the vessel. Gas is drawn off the fluid at the top of the vessel.

To facilitate the escape of gas from the fluid and particularly, gas which is dissolved in the fluid, the vessel is vented to a pressure below that of the pipeline by which the fluid is conducted to the vessel. In the typical application, fluid is permitted to flow into the vessel under pressure, such as pressure supplied by pumps used to convey the fluid, or under field pressure if the fluid is in the form of produced crude oil. Then the input to the the vessel is closed, thus shutting off the pressure within the pipeline leading to the vessel. The vessel may then be vented to atmospheric pressure to thereby allow dissolved gasses to come out of solution and entrained gas bubbles to rise to the surface of the fluid within the vessel and be drawn off.

Subsequently, the vessel is repressured thus driving any remaining bubbles back into solution. This step can be achieved by closing the vent and reopening the input to the fluid flow into the vessel. As an alternative step, a separate source of pressure may be applied to the vessel to raise the pressure within the vessel to a superatmospheric level. While under such superatmospheric pressure fluid flows from the vessel through a sonic apparatus wherein the speed of sound transmission of the fluid passing through the apparatus is measured.

The sonic apparatus provides an upstream and downstream transmitter and receiver. The speed of sound transmission of the fluid is measured in both the upstream and downstream directions. The difference in the upstream and downstream speeds is used to calculate the volumetric flow rate. The sum of the speeds is used to determine the composition, that is, whether water or oil. These calculations can then be used to determine the net volume of water and oil in the flow stream.

The repressured fluid flowing from the vessel through the sonic apparatus will result in any remaining gas bubbles being dissolved into the liquid or compressed to the point wherein their deleterious effect upon the sonic apparatus will be substantially eliminated or at least greatly reduced.

Thus by the sequence of steps employed in the present method, net volume of water and oil in a flow stream can be determined in a manner wherein the necessary measurements are not vitiated by gas otherwise present in the stream.

The basic equipment used to practice the invention includes a combination sonic flowmeter and concentration monitor which measures the velocity of sound between a pair of transducers, one placed upstream of the other already employing a technique well known in the prior art. By alternately measuring upstream and downstream speed of sound by means of upstream and downstream transmissions, the resulting data will yield both flow rate (difference of sound velocities in the two directions) and composition or concentration of water in oil (sum of the sound velocities in the two directions).

BRIEF DESCRIPTION OF THE DRAWING

The drawing illustrates apparatus for practicing the method of the invention including a vessel for receiving fluid from a pipeline and fluid outlet piping from the vessel, the outlet piping including sonic apparatus for detecting the speed of sound transmission and the flow rate of the fluid flowing from the vessel.

DESCRIPTION OF THE PREFERRED EMBODIMENT

Referring now to the drawing an apparatus which may typically be employed in practicing the method of the invention is illustrated. A vessel 10 is shown, supported on legs 12. The vessel has a fluid inlet 14 which receives a pipeline 16. In the typical oil field application of the invention, the pipeline 16 having an inlet valve 17 therein, is connected such as to a manifold wherein the production from a plurality of wells is collected. A gas outlet 18 is connected through a valve 20 to piping 22 which connects to a low pressure area. In some applications the piping 22 may be communicated directly to the atmosphere.

A gauge 24 indicates the pressure within the vessel.

A typical vessel includes a pressure relief pop valve 26 which is merely a safety feature and is not otherwise employed in the invention.

A fluid outlet 28 on the lower end of the vessel connects by piping 30 to a mixer 32 and flow straightener 34. From this the fluid flowing out of the vessel from opening 28 passes through a sonic apparatus 36. The piping 30 then connects through a valve 38 to a discharge pipeline 40.

As an auxiliary apparatus as will be described subsequently, a fluid pressure source 42 connects through a valve 44 to a vessel fluid pressure inlet 46.

The sonic apparatus 36 generally consists of a housing 48 through which fluid flowing through piping 30 passes. The housing includes branch fittings 50 and 52 which contain transducers which generate and receive sound signals. These generated and received sound signals pass through the fluid column flowing within the housing 48. Typically the transducers within the branch fittings 50 and 52 are crystal devices which generate high frequency sound energy when excited by an electrical signal and, in turn, generate an electrical signal upon receipt of sonic energy. These transducers are connected by conductors 54 to sonic flow meter and concentration measurement circuitry 56 which in turn, is connected to computer circuitry 58 and an output indicator or recorder 60. A temperature probe 62 is connected by conductor 64 to the sonic flow meter circuitry 56 for improving the accuracy of the sonic device.

The apparatus described herein is not unlike that of other apparatus which is typically employed in making water cut measurements and the essence of the invention is not in this specific apparatus but in the method employed in making measurements.

As previously indicated, a basic problem in using a sonic apparatus to measure flow rates, or to determine fluid composition, is the deleterious effect on measurements caused by gas bubbles in the fluid. Bubbles drastically affect the speed of sound transmission in fluid and when present in any significant amount, destroy the effectiveness of sonic apparatus for measurement purposes. By practicing the methods hereinafter described, dissolved and entrained gas in liquid, and particularly in crude oil, are dealt with in a manner to solve the problem normally encountered with sonic measurements.

In the typical application of the invention, fluid will flow through open valve 17 to the interior vessel 10. The first step in the method is to permit dissipation of gas which may be dissolved in or entrained in the liquid. For this purpose, a quiescent zone is established by and within the vessel 10. Inlet valve 17 is closed, stopping flow into the vessel thus allowing the fluid within the vessel to settle into a relatively undisturbed state. Gas entrained within the fluid migrates to the surface of the fluid within the vessel and is collected within the upper portion of the vessel 10. Next, valve 20 is opened to depressurize the fluid within vessel 10. The pressure in the vessel is allowed to decrease to a lower pressure, such as to atmospheric pressure. As the fluid pressure decreases, gas (at least a significant portion thereof) dissolved in the fluid will flush off, that is, pass out of solution, and rise to the surface of the fluid to be drawn off through valve 20 and piping 22. Piping 22 may be connected to a source of reduced pressure or to atmosphere as previously described. In any event, the fluid within the vessel 10 is allowed to pass from a higher to a lower pressure permitting dissolved and entrained gasses to be separated from the fluid.

After the collected gas has been vented, valve 20 is closed and the fluid within the vessel is repressurized. For this purpose, a source of pressure 42 is connected through valve 44 to pressure inlet 46. When valve 44 is opened, the pressure of the fluid within vessel 10 is increased. The pressure source 42 may be a gas bottle feeding through a regulator valve or may be gas supplied from a collection line at the site.

The step of repressurization of the fluid in the vessel serves to direct any remaining entrained gas bubbles back into solution in the fluid and to compress any remaining entrained bubbles.

The fluid may then be passed through piping 30 by opening valve 38. The fluid flows through the sonic apparatus 36 wherein the speed of sound transmission and volumetric flow rate are measured.

As previously indicated, a difficulty with the methods previously known is that most crude oil includes quantities of entrained gas. When this entrained gas is in the form of bubbles of any significant size, the bubbles interfere with the transmission of sound through the fluid and thereby provide an erroneous indication of the inherent speed of sound transmission of the fluid. The presence of significant gas bubbles in a fluid stream makes it impractical to use sonic measuring apparatus. However, if the entrained gas is of a relatively low level and if any bubbles within the gas are compressed to a small size then the effect of gas within the fluid is substantially minimized.

Since the apparatus is capable of detecting the characteristics of the fluid flowing through piping 30 and, in addition, determining the volumetric flow rate, the computer circuitry 58 can be employed to calculate the ratio of oil and water. This is possible since the apparatus 36 can not only measure the speed of sound transmission in the fluid but also the fluid flow rate can be measured using standard sonic flow meter techniques, well known in industry.

While the apparatus 36 shows the branch fittings 50 and 52 which receive the sonic tranducers as being above and below the pipe, in the typical application these fittings will be horizontal or within 30 degrees of the horizontal plane.

The static mixer 32 may be a typical Koch mixture, an apparatus readily available in industry and frequently used for thoroughly mixing fluid flowing in a pipeline.

Reference may be had to U.S. Pat. Nos. 4,080,837 and 4,236,406 for information as to the use of sonic flowmeter technology to make volumetric flow measurements and fluid composition detection. In addition, the article "Process Measurements By Sound Velocimeters" in the September, 1970 issue of *Instruments and Control Systems,* pages 112-113, by E. M. Zacharias includes background information of the subject matter to which this invention is directed.

The method described can be employed to provide an indication of the proportion of water and oil in the fluid flowing out of the vessel. In addition, the sonic apparatus can provide the rate of flow of fluid. From these measurements the volumetric percentages of oil and water forming the fluid can be determined. All of these measurements and calculations can be carried out effectively and efficiently as long as the fluid does not include substantial quantities of large gas bubbles to interfere with the speed of sound transmission measurements. The techniques of the present invention as heretofore described enable the measurements to be conducted in such a way as to minimize the effect of gas entrained in the fluid as it flows from a field manifold or other source through a pipeline 16 into the measuring equipment.

While the invention has been described with a great degree of particularity it is manifest that many changes may be made in the details of construction and the arrangement of components without departing from the spirit and scope of this disclosure. It is understood that the invention is not limited to the embodiment set forth herein for purposes of exemplification, but is to be limited only by the attached claim or claims, including the full range of equivalency to which each step thereof is entitled.

What is claimed is:

1. A method of measuring the composition of an oil and water mixture having gas entrained therewith flowing in a pressurized stream, comprising:
   (1) collecting a quantity of the mixture from the pressurized stream in a vessel having a quiescent zone;
   (2) closing off flow from the pressurized stream to the vessel;
   (3) venting pressure from the vessel while the mixture therein is in a quiescent state to permit at least a portion of entrained gas to separate from the mixture;
   (4) repressuring the mixture within the vessel to a superatmospheric pressure;
   (5) passing the mixture from the vessel while subjected to a superatmospheric pressure through a sonic apparatus;
   (6) measuring the speed of sound transmission of the mixture within the sonic apparatus, which speed of sound transmission is indicative of the composition of the mixture; and
   (7) calculating the water and oil composition utilizing the detected speed of sound transmission measurement.

2. The method according to claim 1 wherein the step of venting the vessel while the mixture therein is in a quiescent state includes venting the vessel to the atmosphere.

3. The method of claim 1 including the step of: passing the mixture from the vessel through a mixing apparatus immediately before said step of measuring the speed of sound transmission of the mixture in the sonic apparatus.

4. The method of claim 1 including the step of: passing the mixture from the vessel through a flow straightening apparatus immediately before said step of measuring the speed of sound transmission of the fluid in the sonic apparatus.

5. The method of claim 1 including the step of passing the mixture from the vessel through a mixing and flow straightening apparatus immediately before the step of measuring the speed of sound transmission of the fluid in the sonic apparatus.

6. The method of claim 1 including the step of maintaining the pressure of the mixture to substantially that of the repressured level as the mixture passes from the vessel and until the mixture has passed through the sonic apparatus.

* * * * *